(12) United States Patent
Serra

(10) Patent No.: US 10,870,671 B2
(45) Date of Patent: Dec. 22, 2020

(54) METHOD OF PREPARATION OF ALPHA GALACTOSYL CERAMIDES COMPOUNDS

(71) Applicant: ABIVAX, Paris (FR)

(72) Inventor: Vincent Serra, Bondoufle (FR)

(73) Assignee: ABIVAX, Paris (FR)

( * ) Notice: Subject to any disclaimer, the term of this patent is extended or adjusted under 35 U.S.C. 154(b) by 0 days.

(21) Appl. No.: 14/439,642

(22) PCT Filed: Oct. 30, 2013

(86) PCT No.: PCT/EP2013/072711
§ 371 (c)(1),
(2) Date: Apr. 29, 2015

(87) PCT Pub. No.: WO2014/067995
PCT Pub. Date: May 8, 2014

(65) Prior Publication Data
US 2015/0291646 A1 Oct. 15, 2015

Related U.S. Application Data

(60) Provisional application No. 61/720,098, filed on Oct. 30, 2012.

(30) Foreign Application Priority Data

Oct. 30, 2012 (EP) .................... 12306355

(51) Int. Cl.
*C07H 15/26* (2006.01)
*C07H 15/04* (2006.01)
*C07D 317/28* (2006.01)
*C07H 15/18* (2006.01)
*C07H 15/06* (2006.01)

(52) U.S. Cl.
CPC .......... *C07H 15/26* (2013.01); *C07D 317/28* (2013.01); *C07H 15/04* (2013.01); *C07H 15/06* (2013.01); *C07H 15/18* (2013.01)

(58) Field of Classification Search
CPC ...... C07H 14/04; C07H 14/26; C07H 317/28; C07H 15/18
USPC .............................. 536/17.9, 18.5
See application file for complete search history.

(56) References Cited

U.S. PATENT DOCUMENTS 3,664,998 A 5/1972 Bannister

FOREIGN PATENT DOCUMENTS

| CN | 1405172 A | 3/2003 |
| CN | 101012254 A | 8/2007 |
| DE | 2053667 | 5/1971 |
| EP | 0 028 917 A2 | 5/1981 |
| RU | 2 141 944 C1 | 11/1999 |
| WO | WO 2007/050668 A1 | 5/2007 |
| WO | WO 2007/118234 A2 * | 10/2007 ........... A61K 31/739 |
| WO | WO 2012/094540 A2 | 7/2012 |

OTHER PUBLICATIONS

Pajk et al, Organic & Biomolecular Chemistry, 2011, 9, 4150-4159.*
Smith, J.G., Organic Chemistry, 2009, pp. 975-976.*
Noti et al, Chemistry: A European Journal, 2006, 12, 8664-8686.*
Greene et al, Protective Groups in Organic Synthesis, John Wiley, 2nd Ed., 1991, pp. 315-322, 327-328, 338-339, 355-356, 364-365 and 379-381.*
Pajk, et al. 2011 "Nitroxide-fluorophore double probes: a potential tool for studying membrane heterogeneity by ESR and fluorescence" *Organic & Biomolecular Chemistry* 9(11); 4150-4159.
Chen, et al. 2004 "Efficient synthesis of α-C-galactosyl ceramide immunostimulants: Use of ethylene-promoted olefin cross-metathesis" *Organic Letters* 6(22): 4077-4080.

(Continued)

*Primary Examiner* — Ganapathy Krishnan
(74) *Attorney, Agent, or Firm* — Knobbe, Martens, Olson & Bear, LLP

(57) ABSTRACT

The present invention relates to a method of preparation of α-galactosyl ceramides compounds of formula (I):

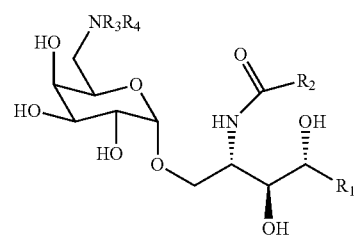

comprising a step a) of glycosylation of a compound of formula (II):

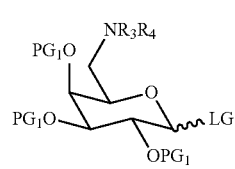

with a compound of formula (III):

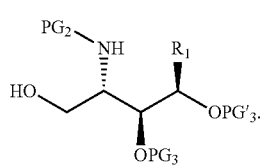

12 Claims, No Drawings

(56) References Cited

OTHER PUBLICATIONS

Chen, et al. 2006 "E and Z α-C-Galactosylceramides by Julia-Lythgoe-Kocienski Chemistry: A test of the receptor-binding model for glycolipid immunostimulants" *ChemBioChem* 7: 1017-1022.

Hasegawa, et al. 1973 "Synthetic studies on amino-α-glycosides of aminocyclitols. Synthesis of kanamycin analogues" *Carbohydrate Research* 30: 319-325.

Hsieh, et al. 2012 "Synthesis and evaluation of acyl-chain- and galactose-6"-modified analogues of α-GalCer for NKT cell activation" *ChemBioChem* 13: 1689-1697.

Jervis, et al. 2011 "Synthesis of a versatile building block for the preparation of 6-N-derivatized α-galactosyl ceramides: rapid access to biologically active glycolipids" *The Journal of Organic Chemistry* 76: 320-323.

Liu, et al. 2008 "Synthesis of diglycosylceramides and evaluation of their iNKT cell stimulatory properties" *Bioorganic & Medicinal Chemistry Letters* 18: 3052-3055.

Tsai, Meng-Shen and Lee, Zhong-Jun 2006 in *Carbohydrate Chemistry (Basis, Reaction, Synthesis, Separation, and Structure)*, Published by Chemical Industry Press, Beijing, pp. 59-60.

Pauwels, et al. 2012 "Synthesis of 6"-triazole-substituted α-GalCer analogues as potent iNKT cell stimulating ligands" *Bioorganic & Medicinal Chemistry* 20: 7149-7154.

Sun, et al. 2004 "An efficient preparation of isosteric phosphonate analogues of sphingolipids by opening of oxirane and cyclic sulfamidate intermediates with α-lithiated alkylphosphonic esters" *The Journal of Organic Chemistry* 69: 7694-7699.

Ueno, et al. 1967 "Synthetic studies on carbohydrate antibiotics" *Agr. Biol. Chem.* 31(11): 1346-1350.

Xia, et al. 2009 "Facile synthesis of biotin-labelled α-galactosylceramide as antigen for invariant natural killer T cells" *Tetrahedron* 65: 6390-6395.

Mengshen, et al. 2007 "Fundamentals, Reaction, Synthesis, Separation and Structure" *Carbohydrate Chemistry* in 9 pages, including English translation.

Noti, et al. 2006 "Preparation and use of microarrays containing synthetic heparin oligosaccharides for the rapid analysis of heparin-protein interactions" *Chemistry: A European Journal* 12: 8664-8686.

Smith, et al. 2009 in *Organic Chemistry*, Third Edition, McGraw Hill; 25.11 "Amines as Nucleophiles" pp. 975-976.

* cited by examiner

METHOD OF PREPARATION OF ALPHA GALACTOSYL CERAMIDES COMPOUNDS

FIELD OF THE INVENTION

The present invention relates to a method of preparation of a class of 6″-deoxy-6-amino α-galactosyl ceramides.

BACKGROUND OF THE INVENTION

The interests lying in α-galactosyl ceramides compounds (also called α-GCs compounds) are well explained in WO 2007/118234, inter alia. α-GCs compounds have been found to effectively stimulate natural killer T (NKT) cells, both in vitro and in vivo. NKT cells have been implicated in suppression of autoimmunity and graft rejection, promotion of resistance to pathogens, and promotion of tumor immunity.

A natural glycolipid molecule, termed KRN7000, is known to stimulate NKT cells when loaded into CD1d tetramers. However, supplies of KRN7000, which is derived from a marine sponge, have been limited and this glycolipid has relatively poor solubility in either aqueous or organic solvents.

Thus, a method of preparation of a modified α-GC compound ((15Z)-N-[(1S,2S,3R)-1-[[[6-(acetylamino)-6-deoxy-α-D-galactopyranosyl]oxy]methyl]-2,3-dihydroxyheptadecyl]-15-tetracosenamide), also called PBS-57, has been developed (synthesis described in WO 2007/118234).

Said method involves the coupling of a fluoro-sugar derivative (A), with a phytosphingosine moiety (B) comprising an acyl unsaturated side-chain, as represented in the following scheme:

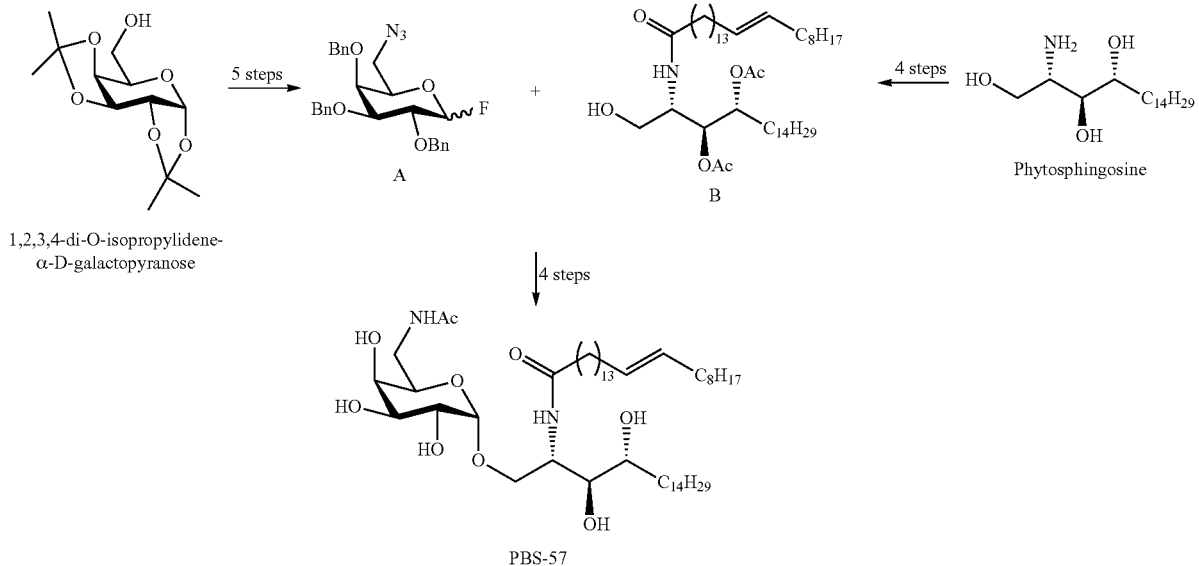

PBS-57

However, the method according to WO 2007/118234 presents several drawbacks and may be difficult to implement at an industrial scale. Indeed, it involves the use of toxic, hazardous and/or expensive reagents, such as $AgClO_4$, $SnCl_2$, $PPh_3$, DIAD (diisopropyl azodicarboxylate), DAST (diethylaminosulfur trifluoride), hydrofluoric acid, DCC (N,N′-dicyclohexylcarbodiimide), and sodium. Furthermore, at least 11 steps of purification by silica-gel column chromatography are necessary to provide with the final product PBS-57.

These points represent major obstacles to the scale-up of the method according to WO 2007/118234.

Thus, there is a need of developing an efficient, flexible, less expensive and safe method of preparation of α-GCs compounds.

SUMMARY OF THE INVENTION

One of the aims of the present invention is to provide a method of preparation of α-GC compounds avoiding the use of toxic, hazardous and/or expensive reagents.

Another aim of the present invention is to provide a method of preparation of α-GC compounds wherein the number of steps is limited.

Another aim of the present invention is to provide a method of preparation of α-GC compounds wherein the number of purification steps is limited, particularly the number of silica-gel column chromatography purification steps.

The present invention relates to a method of preparation of a compound of formula (I):

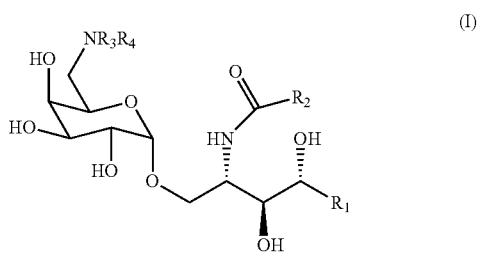

comprising a step a) of glycosylation, preferably in the presence of a Lewis acid, of a compound of formula (II)

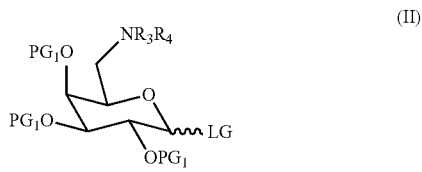

with a compound of formula (III):

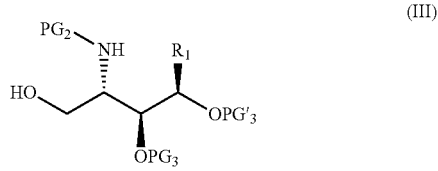

said step a) providing a compound of formula (IV):

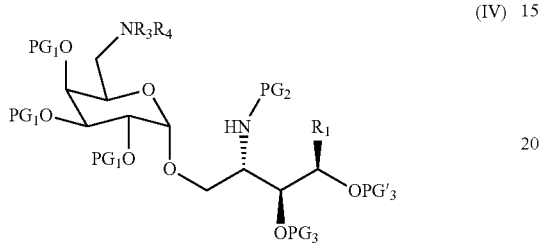

wherein:
$R_1$ represents a linear or branched, saturated or unsaturated $C_1$-$C_{20}$ alkyl group, optionally substituted;
$R_2$ represents a linear or branched, saturated or unsaturated $C_1$-$C_{30}$ alkyl group, optionally substituted;
$R_3$ represents $C_1$-$C_6$ alkyl, a $C_3$-$C_6$ cycloalkyl, a $C_1$-$C_6$ acyl or a benzoyl group; and $R_4$ represents H or $C_1$-$C_6$ alkyl group; or
$R_3$ and $R_4$ form together with the nitrogen atom to which they are attached a $C_2$-$C_6$ heterocycloalkyl group or a $C_1$-$C_5$ heteroaryl group;
$PG_1$ represents a hydroxyl function protecting group;
$PG_2$ represents a primary amine function protecting group;
$PG_3$ represents a hydroxyl function protecting group;
$PG'_3$ represents a hydroxyl function protecting group, optionally forming, together with $PG_3$ and the oxygen and carbon atoms to which they are connected, a $C_3$-$C_6$ heterocycloalkyl, optionally substituted; and
LG represents a leaving group.

The compounds according to formula (I) are α-galactosyl ceramide derivatives, comprising a sugar moiety and a lipid moiety.

The sugar moiety is a galactose-type fragment.
The lipid moiety is a ceramide-type fragment.
The galactose-type sugar moiety and the ceramide-type lipid moiety of the compounds according to the invention are connected together through the step a) of glycosylation, via the formation of a glycosidic bond, at the C-1 position of the galactose moiety.

The mechanism of step a) may be described as follows.
The glycosylation reaction of step a) involves the coupling, via the formation of a glycosidic bond, of a glycosyl donor, represented by compound of formula (II), with a glycosyl acceptor, represented by compound of formula (III).

The glycosyl donor is a sugar derivative with a suitable leaving group—LG at the C-1 position, also called anomeric position. This leaving group may be activated and eliminated under the reaction conditions of step a), therefore leaving an electrophilic anomeric carbon under the form of an oxocarbenium ion.

The term "leaving group" refers to a molecular fragment that departs with a pair of electrons in heterolytic bond cleavage. Preferably, leaving group—LG departs from compound of formula (II) into an anionic or neutral molecule. Leaving groups are for example sulfonates such as triflate, tosylate and mesylate, halides such as iodide, bromide, chloride and fluoride, nitrates, phosphates and imidates, such as acetimidate optionally substituted by halogen atoms.

The term "acetimidate" refers to a group of formula:

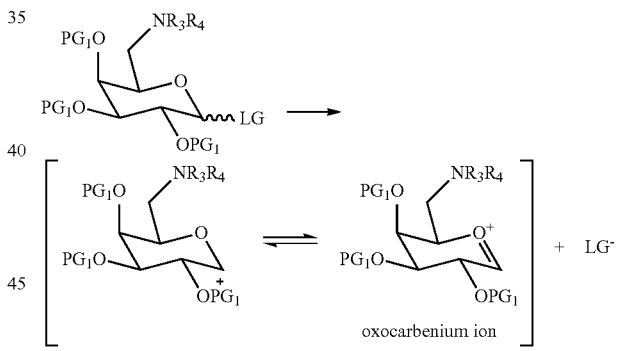

wherein $R_i$, $R_{ii}$ and $R_{iii}$, identical or different, are chosen from the group consisting of a hydrogen atom, a chlorine atom, a fluorine atom and a methyl group. According to one embodiment, $R_i$, $R_{ii}$ and $R_{iii}$ are identical and represent a chlorine atom.

DETAILED DESCRIPTION OF THE PREFERRED EMBODIMENT

According to one embodiment, step a) is carried out in the presence of an activator which promotes the cleavage of the carbon-LG bond and the leaving of leaving group—LG, which results in the formation of the below-represented oxocarbenium ion.

According to one embodiment, the activator of the glycosylation reaction of step a) is chosen from the Lewis acids, for example from TMSOTf (trimethylsilyl trifluoromethanesulfonate) and $BF_3 \cdot Et_2O$.

According to one embodiment, the activator is TMSOTf.
According to one embodiment, step a) is carried out in an anhydrous solvent or mixture of solvents, for example in a mixture of tetrahydrofuran and diethylether.

According to one embodiment, step a) is carried out at low temperature, for example from 0° C. to −78° C., preferably from 0° C. to −20° C. The low temperature advantageously limits the formation of by-products.

According to one embodiment, step a) is carried out in the presence of activated 4 Å molecular sieves. Molecular sieves advantageously enable the trapping of water.

According to one embodiment, the activator is added to a mixture of compound of formula (II) and compound of formula (III) at low temperature, for example from 0° C. to −40° C., preferably at −20° C. The resulting mixture is then stirred around the same temperature, for at least one hour.

According to one embodiment, leaving group—LG of formula (II) is an acetimidate group. The use of acetimidate provides many advantages including ease of formation and reactivity.

According to one embodiment, leaving group—LG of formula (II) is a trichloroacetimidate group.

As compounds of formula (II), one may cite the compounds having the following formula (II-1):

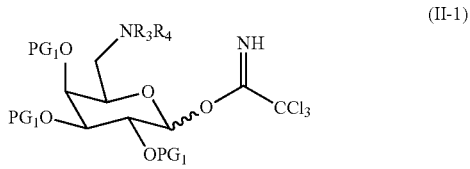

(II-1)

wherein $PG_1$, $R_3$, and $R_4$ are as defined above in formula (II).

The glycosyl acceptor is a compound comprising an unprotected nucleophilic hydroxyl group —OH which may attack the carbon of the oxocarbenium ion formed after the leaving of —LG, and allows for the formation of the glycosidic bond, therefore yielding compound of formula (IV).

The reaction conditions of step a) are such that the protecting groups $PG_1$, $PG_2$, $PG_3$ and $PG'_3$ remain unchanged.

Regarding $PG_1$, the term "hydroxyl function protecting group" refers to a group able to protect a free hydroxyl function —OH from reacting during at least one step of a synthesis. Hydroxyl function protecting groups are for example acetyl (Ac), benzyl (Bn), benzoyl (Bz), methoxyethoxymethyl ether (MEM), dimethoxytrityl, methoxymethyl ether (MOM), methoxytrityl, p-methoxybenzyl ether (PMB), methylthiomethyl ether, pivaloyl (Piv), tetrahydropyranyl (THP), trityl (Tr) and silyl ether, such as trimethylsilyl (TMS), tert-butyldimethylsilyl (TBDMS), tri-isopropylsilyloxymethyl (TOM) and triisopropylsilyl (TIPS).

$PG_1$ protecting groups aim at protecting the hydroxyl groups of the galactose moiety during step a), and optionally during the steps of preparation of compound of formula (II).

The protecting group $PG_1$ is for example a benzyl group, optionally substituted.

According to one embodiment, $PG_1$ is a group of formula —$CH_2$-Ph.

Generally, the deprotection of such protecting groups is carried out by hydrogenolysis, in the presence of a metal catalyst, for example a palladium catalyst.

As compounds of formula (II), one may cite the compounds having the following formula (II-2):

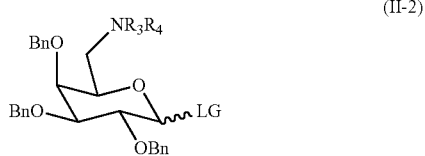

(II-2)

wherein LG, $R_3$, and $R_4$ are as defined above in formula (II).

As compounds of formula (II-2), one may cite the compounds having the following formula (II-3):

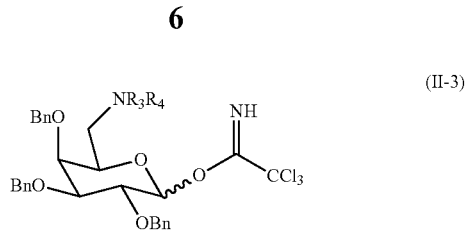

(II-3)

wherein $R_3$ and $R_4$ are as defined above in formula (II).

Regarding $PG_2$, the term "primary amine function protecting group" refers to a group able to protect a free amino function —$NH_2$ from reacting during at least one step of a synthesis. Primary amine function protecting groups are for example carboxybenzyl (Cbz), p-methoxybenzyl carbonyl (Moz or MeOZ), tert-butyloxycarbonyl (BOC), 9-fluorenylmethyloxycarbonyl (FMOC), acetyl (Ac), benzoyl (Bz), benzyl (Bn), carbamate groups, p-methoxybenzyl (PMB), 3,4-dimethoxybenzyl (DMPM), p-methoxyphenyl (PMP), tosyl (Ts) and other sulfonamides (Nosyl & Nps) groups.

$PG_2$ protecting group aims at protecting the amino group of the lipid moiety during step a), and optionally during the steps of preparation of compound of formula (III).

The protecting group $PG_2$ is for example a carboxybenzyl group, optionally substituted.

Generally, the deprotection of such protecting groups is carried out in acidic conditions, in the presence of an acid, such as HCl, in a solvent chosen from lower alcohol solvents.

According to one embodiment, $PG_2$ is a group of formula —C(O)OCH$_2$-Ph.

As compounds of formula (III), one may cite the compounds having the following formula (III-1):

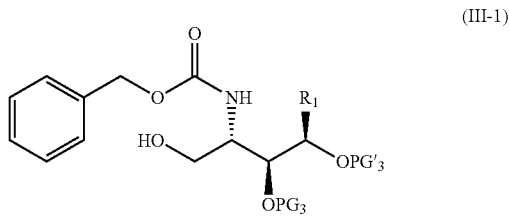

(III-1)

wherein $R_1$, $PG_3$ and $PG'_3$ are as defined above in formula (III).

Regarding $PG_3$ and $PG'_3$, the term "hydroxyl function protecting group" refers to a group able to protect a free hydroxyl function —OH from reacting during at least one step of a synthesis. Examples of such groups are given above.

$PG_3$ and $PG'_3$ protecting groups aim at protecting the hydroxyl groups of the lipid moiety during step a), and optionally during the steps of preparation of compound of formula (III), and optionally during the step of introduction of group $R_2$.

Protecting groups $PG_3$ and $PG'_3$ aim at protecting two vicinal hydroxyl functions, forming a 1,2-diol moiety. This kind of diol group is generally protected via the formation of an acetal group, for example a heterocyclic acetal group. Examples of 1,2-diol protecting groups are for example acetonide (also called isopropylidene acetal) and benzylidene acetal.

Generally, the deprotection of such protecting groups is carried out in acidic conditions, in the presence of an acid, such as HCl, in a solvent chosen from lower alcohol solvents.

According to one embodiment, protecting groups PG$_3$ and PG'$_3$ form together with the two oxygen atoms to which they are connected, an isopropylidene acetal group.

As compounds of formula (III), one may cite the compounds having the following formula (III-2):

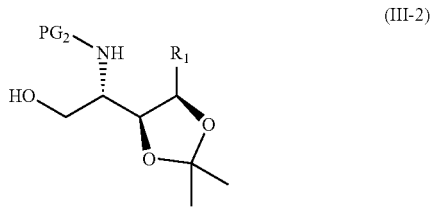

(III-2)

wherein R$_1$ and PG$_2$ are as defined above in formula (III).

As compounds of formula (III-1) and of formula (III-2), one may cite the compounds having the following formula (III-3):

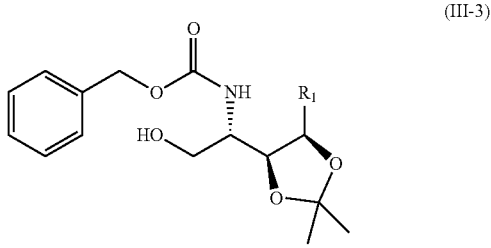

(III-3)

wherein R$_1$ is as defined above in formula (III).

According to one embodiment, PG$_1$ is —CH$_2$-Ph, also called -Bn or benzyl group.

As compounds of formula (IV), one may cite the compounds having the following formula (IV-1):

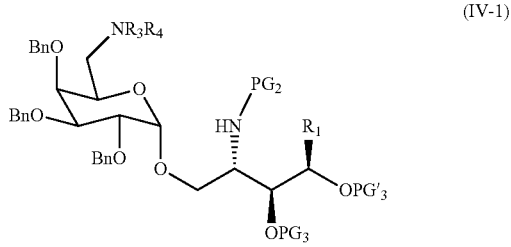

(IV-1)

wherein R$_1$, R$_3$, R$_4$, PG$_2$, PG$_3$ and PG'$_3$ are as defined above in formula (IV).

According to one embodiment, PG$_2$ is —C(O)OCH$_2$Ph, also called carboxybenzyl group.

As compounds of formula (IV), one may cite the compounds having the following formula (IV-2):

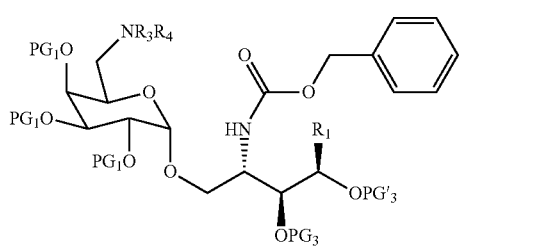

(IV-2)

wherein R$_1$, R$_3$, R$_4$, PG$_1$, PG$_3$ and PG'$_3$ are as defined above in formula (IV).

According to one embodiment, protecting groups PG$_3$ and PG'$_3$ form together with the two oxygen atoms to which they are connected, an isopropylidene acetal group.

As compounds of formula (IV), one may cite the compounds having the following formula (IV-3):

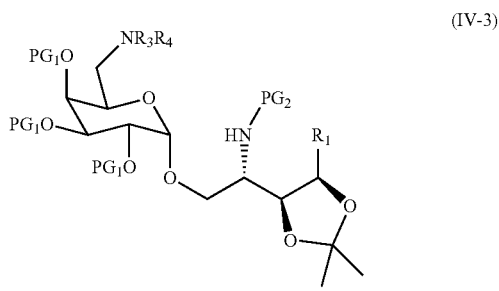

(IV-3)

wherein R$_1$, R$_3$, R$_4$, PG$_2$, PG$_3$ and PG'$_3$ are as defined above in formula (IV).

As compounds of formula (IV), one may cite the compounds having the following formula (IV-4):

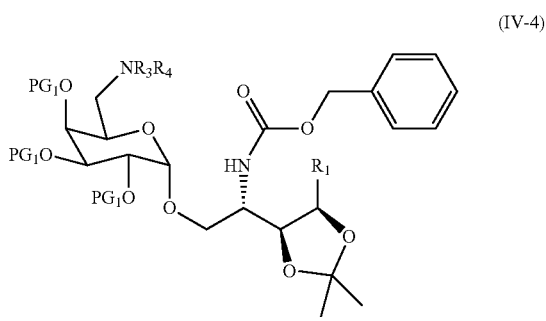

(IV-4)

wherein R$_1$, R$_3$, R$_4$ and PG$_1$ are as defined above in formula (IV).

As compounds of formula (IV), one may cite the compounds having the following formula (IV-5):

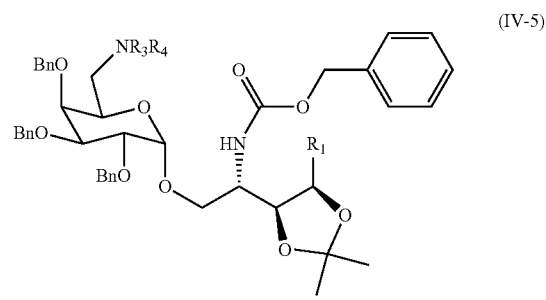

(IV-5)

wherein R$_1$, R$_3$ and R$_4$ are as defined above in formula (IV).

According to one embodiment, the compound of formula (I) is obtained from a compound of formula (IV), obtained by step a), via the deprotection of protecting groups PG$_1$, PG$_2$, PG$_3$ and PG'$_3$, and the coupling with a compound of formula R$_2$COCl (VII), R$_2$ being as defined in formula (I).

Protecting groups PG$_1$, PG$_2$, PG$_3$ and PG'$_3$ may be deprotected either sequentially or simultaneously.

According to one embodiment, PG$_1$ and PG$_2$ are deprotected simultaneously, i.e. in the same step, preferably in the same pot.

According to one variant of the method according to the invention, protecting groups $PG_1$ and $PG_2$ are deprotected simultaneously from a compound of formula (IV), while protecting groups $PG_3$ and $PG'_3$ remain unchanged.

According to this variant, the method of the invention comprises, after step a), a step b) of deprotection of the protecting groups $PG_1$ and $PG_2$ of a compound of formula (IV), preferably by hydrogenolysis in the presence of a metal catalyst, said step b) providing a compound of formula (V):

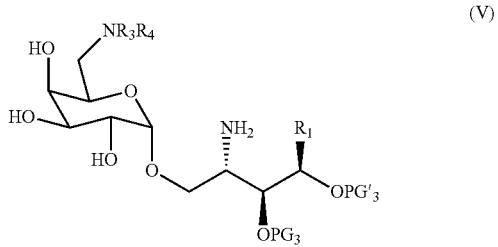

wherein $R_1$, $R_3$, $R_4$, $PG_3$ and $PG'_3$ are as defined above in formula (IV).

As compounds of formula (V), one may cite the compounds having the following formula (V-1):

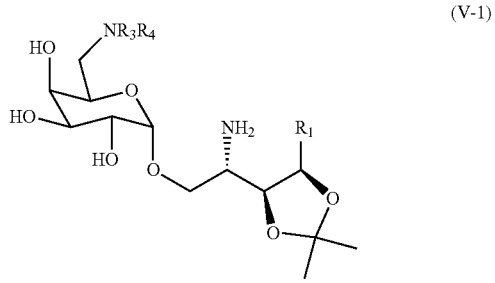

wherein $R_1$, $R_3$ and $R_4$ are as defined above in formula (V).

According to one embodiment, step b) is carried out in the presence of $H_2$ and a palladium catalyst, for example $Pd(OH)_2$ on charcoal.

According to one embodiment, step b) is carried out in a mixture of dichloromethane and methanol.

According to one embodiment, step b) is carried out at room temperature.

According to this variant, the method of the invention comprises after step b):
- a step c) of coupling of a compound of formula (V), obtained by step b), with a compound of formula $R_2COCl$ (VII), in the presence of a base, and
- a step d) of deprotection of the protecting groups $PG_3$ and $PG'_3$ of the product obtained in step c),
said steps providing a compound of formula (I).

According to one embodiment, step c) is carried out in the presence of an organic base, for example a tertiary amine such as triethylamine.

According to one embodiment, step c) is carried out in the presence of a polar solvent, such as tetrahydrofuran.

According to one embodiment, step c) is carried out at room temperature, for at least one hour.

According to one embodiment, step c) is carried out in the presence of an acid, such as HCl, for example in isopropanol.

The step d) is preferably carried out in the presence of a mixture of dichloromethane and methanol.

According to one embodiment, step c) is carried out at a temperature comprised from 20° C. to 60° C., preferably around 40° C., preferably for at most one hour.

According to another variant of the method according to the invention, protecting groups $PG_1$, $PG_2$, $PG_3$ and $PG'_3$ are deprotected simultaneously, i.e. within the same step, but not necessarily in the same pot.

According to this other variant, the method of the invention comprises, after step a), a step b') of deprotection of the protecting groups $PG_1$, $PG_2$, $PG_3$ and $PG'_3$ of a compound of formula (IV), preferably by hydrogenolysis in the presence of a metal catalyst, optionally followed by a treatment in acidic conditions, said step b') providing a compound of formula (VI):

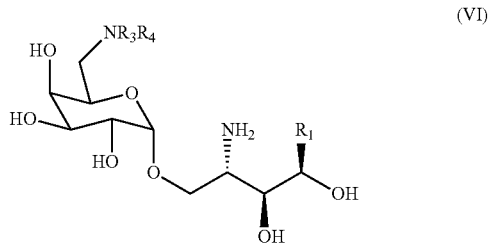

wherein $R_1$, $R_3$ and $R_4$ are as defined above in formula (IV).

According to one embodiment, step b') is carried out in the presence of $H_2$ and a palladium catalyst, for example $Pd(OH)_2$ on charcoal.

According to one embodiment, step b') is carried out in a mixture of dichloromethane and methanol.

According to one embodiment, step b') is carried out at room temperature, for at least one hour.

According to one embodiment, further to the hydrogenolysis, step b') optionally comprises another step of treatment in acidic conditions, in the presence of an acid, such as HCl, for example in isopropanol.

According to one embodiment, said treatment in acidic conditions is carried out in the presence of a mixture of dichloromethane and methanol.

According to one embodiment, said treatment in acidic conditions is carried out at a temperature comprised from 20° C. to 60° C., preferably around 40° C., for at most one hour.

According to this other variant, the method of the invention comprises, after step b'), a step c') of coupling of a compound of formula (VI) with a compound of formula $R_2COCl$ (VII), in the presence of a base, said step c') providing a compound of formula (I).

According to one embodiment, the step c') is carried out in the presence of an organic base, for example a tertiary amine such as triethylamine.

According to one embodiment, the step c') is carried out in the presence of a polar solvent, such as tetrahydrofuran.

According to one embodiment, the step c') is carried out at room temperature, for at least one hour.

According to one embodiment, $R_1$ and $R_2$ represent long-chain aliphatic groups, saturated or unsaturated, comprising at least 10 carbon atoms, optionally substituted.

In the formula (I) according to the invention, $R_1$ represents a linear or branched, saturated or unsaturated $C_1$-$C_{20}$ alkyl group, optionally substituted.

According to one embodiment, $R_1$ is a linear group.

According to one embodiment, $R_1$ is a saturated group.

According to one embodiment, $R_1$ is a non substituted group.

According to one embodiment, $R_1$ is a linear saturated alkyl group comprising from 1 to 20 carbon atoms.

According to one embodiment, $R_1$ comprises from 6 to 20 carbon atoms.

According to one embodiment, $R_1$ comprises from 12 to 20 carbon atoms.

According to one embodiment, $R_1$ comprises 14 carbon atoms.

$R_1$ is for example a linear saturated —$C_{14}H_{29}$ group.

As compounds of formula (I), one may cite the compounds having the following formula (I-1):

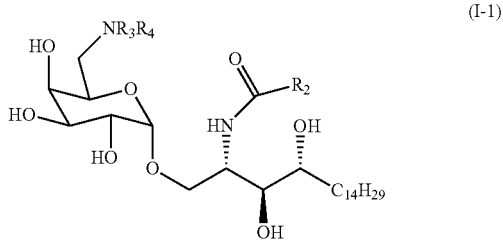

(I-1)

wherein $R_2$, $R_3$ and $R_4$ are as defined above in formula (I).

In the formula (I) according to the invention, $R_2$ represents a linear or branched, saturated or unsaturated $C_1$-$C_{30}$ alkyl group, optionally substituted.

According to one embodiment, $R_2$ is a linear group.

According to one embodiment, $R_2$ is a saturated group.

According to one embodiment, $R_2$ is a non substituted group.

According to one embodiment, $R_2$ is a linear saturated alkyl group comprising from 1 to 30 carbon atoms.

According to one embodiment, $R_2$ comprises from 6 to 30 carbon atoms.

According to one embodiment, $R_2$ comprises from 12 to 30 carbon atoms.

According to one embodiment, $R_2$ comprises 23 carbon atoms.

$R_2$ is for example a linear saturated —$C_{23}H_{47}$ group.

As compounds of formula (I), one may cite the compounds having the following formula (I-2):

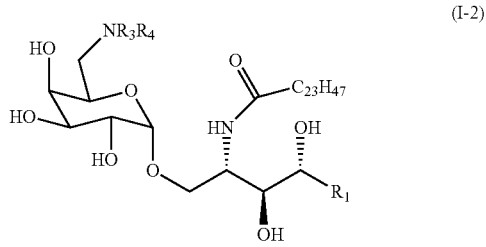

(I-2)

wherein $R_1$, $R_3$ and $R_4$ are as defined above in formula (I).

As compounds of formula (I), one may cite the compounds having the following formula (I-3):

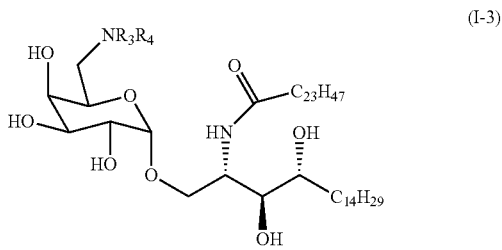

(I-3)

wherein $R_3$ and $R_4$ are as defined above in formula (I).

The term "alkyl" means a saturated or unsaturated aliphatic hydrocarbon group which may be straight or branched having 1 to 30 carbon atoms in the chain. "Branched" means that one or lower alkyl groups such as methyl, ethyl or propyl are attached to a linear alkyl chain. The alkyl may be substituted with one or more "alkyl group substituents" which may be the same or different, and include for instance halo, cycloalkyl, hydroxy (OH), alkoxy, amino ($NH_2$), carboxy (COOH).

The term "alkoxy" refers to an —O-alkyl radical.

The term "cycloalkyl" as employed herein includes saturated monocyclic hydrocarbon groups having 3 to 6 carbon atoms, wherein any ring atom capable of substitution may be substituted by a substituent. Examples of cycloalkyl moieties include, but are not limited to, cyclohexyl and cyclopentyl.

The term "halo" refers to the atoms of the group 17 of the periodic table (halogens) and includes in particular fluorine, chlorine, bromine, and iodine atom.

The term "aryl" refers to an aromatic monocyclic, bicyclic, or tricyclic hydrocarbon ring system, wherein any ring atom capable of substitution may be substituted by a substituent. Examples of aryl moieties include, but are not limited to, phenyl, naphthyl, and anthracenyl.

The term "heterocycloalkyl" refers to a nonaromatic 5-7 membered monocyclic, ring system having 1-3 heteroatoms and 2-6 carbon atoms, said heteroatoms being selected from O, N, or S (e. g., carbon atoms and 1-3 heteroatoms of N, O, or S), wherein any ring atom capable of substitution may be substituted by a substituent.

The term "substituents" refers to a group "substituted" on an alkyl, heterocycloalkyl or aryl group at any atom of that group. Suitable substituents include, without limitation, alkyl, alkenyl, alkoxy, halo, hydroxy, cyano, nitro, amino, $SO_3H$, ester, amide, unsubstituted aryl, unsubstituted heteroaryl, unsubstituted heterocycloalkyl, and unsubstituted cycloalkyl.

The term "heteroaryl" refers to an aromatic 5-6 membered monocyclic ring system having 1-4 heteroatoms and 1-5 carbon atoms, said heteroatoms selected from O, N, or S (e. g., carbon atoms and 1-3heteroatoms of N, O, or S), wherein any ring atom capable of substitution may be substituted by a substituent. As heteroaryl, one may cite pyridyl, pyrrolyl, pyrazolyl, imidazolyl, oxazolyl, isoxazolyl, thiazolyl, isothiazolyl, triazolyl, furazanyl, tetrazolyl, diazinyl, triazinyl, tetrazinyl.

In the reactions described hereinafter, it may be necessary to protect reactive functional groups, for example hydroxy, amino, imino, thio or carboxy groups, where these are desired in the final product, to avoid their unwanted participation in the reactions. Conventional protecting groups may be used in accordance with standard practice, for examples see T. W. Greene and P. G. M. Wuts in *Protective Groups in Organic Chemistry*, John Wiley and Sons, 1991; J. F. W. McOmie in *Protective Groups in Organic Chemistry*, Plenum Press, 1973.

Some reactions may be carried out in the presence of a base. There is no particular restriction on the nature of the base to be used in this reaction, and any base conventionally used in reactions of this type may equally be used here, provided that it has no adverse effect on other parts of the molecule. Examples of suitable bases include: sodium hydroxide, potassium carbonate, triethylamine, alkali metal hydrides, such as sodium hydride and potassium hydride; alkyllithium compounds, such as methyllithium and butyllithium; and alkali metal alkoxides, such as sodium methoxide and sodium ethoxide.

Usually, reactions are carried out in a suitable solvent. A variety of solvents may be used, provided that it has no adverse effect on the reaction or on the reagents involved. Examples of suitable solvents include: hydrocarbons, which may be aromatic, aliphatic or cycloaliphatic hydrocarbons, such as hexane, cyclohexane, benzene, toluene and xylene; amides, such as N,N-dimethylformamide; alcohols such as ethanol and methanol and ethers, such as diethyl ether, methyl tert-butyl ether and tetrahydrofuran.

The reactions can take place over a wide range of temperatures. In general, we find it convenient to carry out the reaction at a temperature of from 0° C. to 150° C. (more preferably from about room temperature to 100° C.). The time required for the reaction may also vary widely, depending on many factors, notably the reaction temperature and the nature of the reagents. However, provided that the reaction is effected under the preferred conditions outlined above, a period of from 3 hours to 20 hours will usually suffice.

The compound thus prepared may be recovered from the reaction mixture by conventional means. For example, the compounds may be recovered by distilling off the solvent from the reaction mixture or, if necessary, after distilling off the solvent from the reaction mixture, pouring the residue into water followed by extraction with a water-immiscible organic solvent and distilling off the solvent from the extract. Additionally, the product may, if desired, be further purified by various well-known techniques, such as recrystallization, reprecipitation or the various chromatography techniques, notably column chromatography or preparative thin layer chromatography.

According to one embodiment, in the compounds according to the invention, $R_3$ is an acyl group, advantageously of formula —C(O)CH$_3$, also called acetyl group.

According to one embodiment, in the compounds according to the invention, $R_4$ is H.

According to one embodiment, in the compounds according to the invention, $R_3$ and $R_4$ form together with the nitrogen atom to which they are attached a $C_1$-$C_5$ heteroaryl group, for example a pyridyl group.

The term "acyl" refers to an alkylcarbonyl, cycloalkylcarbonyl, arylcarbonyl, heterocycloalkylcarbonyl, or heteroarylcarbonyl group, any of which may be further substituted, for example by a group chosen from the group consisting in alkyl and halogen atoms.

Preparation of the Compound of Formula (II)

According to one embodiment, the compound of formula (II) is obtained, via the introduction of leaving group—LG, from a compound of formula (VIII):

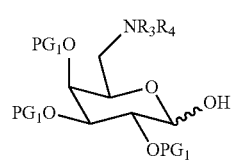

wherein $R_3$, $R_4$ and $PG_1$ are as defined in formula (II).

According to one embodiment, the compound of formula (II-1), wherein LG is a trichloroacetimidate, is obtained from a compound of formula (VIII), in the presence of $CCl_3CN$ and a base, for example $K_2CO_3$, in a solvent, such as dichloromethane. This step is preferably carried out at room temperature, for at least one hour, preferably for at least 12 hours.

According to one embodiment, the compound of formula (VIII) is obtained from a compound of formula (IX):

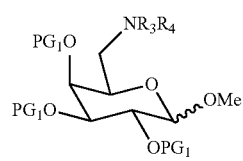

via a step of treatment in the presence of an acidic aqueous solution, comprising for example HCl and acetic acid, preferably by heating at a temperature comprised from 50° C. to 100° C., wherein $R_3$, $R_4$ and $PG_1$ are as defined in formula (VIII).

According to one embodiment, the compound of formula (IX) is obtained from a compound of formula (X):

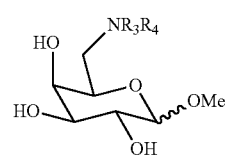

via a step of protection of the free hydroxyl groups by protecting groups $PG_1$, wherein $R_3$, $R_4$ and $PG_1$ are as defined in formula (VIII).

According to one embodiment, the compound of formula (X) is obtained from a compound of formula (XI):

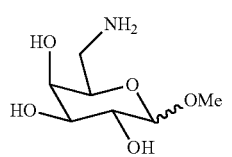

via a step of functionalization of the free amino group by $R_3$ and $R_4$ groups, wherein $R_3$ and $R_4$ are as defined in formula (VIII).

According to one embodiment, the compound of formula (XI) is obtained from a compound of formula (XII):

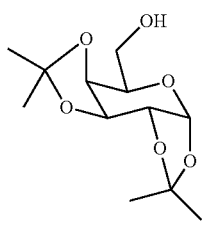
(XII)

according to the procedure described in R. S. Tipson, Methods Carbohydr. Chem., 1963, 2, 246-250.

Compound (XII) is called 1,2,3,4-di-O-isopropylidene-α-D-galactopyranose, and is commercially available, notably from Indofine Chemical Company.

Compound (XI) can be obtained from compound (XII) according to the following procedure. Compound (XII) is treated with tosylchloride in dichloromethane with triethylamine and dimethylamino pyridine to give the corresponding tosylate in 91% yield. The tosylate is treated with potassium phthalimide in DMSO with tetrabutylammonium iodide to give the corresponding phthalimide in approximately 100% yield. The phthalimide is treated with acetyl chloride in methanol to cause deprotection of the alcohols and formation of the methyl glycoside in 87% yield. The amine (XI) is then liberated by treating the phthalimide with hydrazine in ethanol.

The preparation of compounds of formula (IX) from compound of formula (XII) can also be adapted from the method described in Zhou, X. T.; Forestier, C.; Goff, R. D.; Li, C.; Teyton, L.; Bendelac, A.; Savage, P. B. Org. Lett. 2002, 4, 1267-1270.

Preparation of the Compound of Formula (III)

According to one embodiment, the compound of formula (III) is obtained from a compound of formula (XIII):

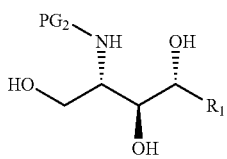
(XIII)

via a step of protection of the two vicinal hydroxyl groups by protecting groups $PG_3$ and $PG'_3$,
wherein $R_1$, $PG_2$, $PG_3$ and $PG'_3$ are as defined in formula (III).

According to one embodiment, the compound of formula (XIII) is obtained from a compound of formula (XIV) of formula:

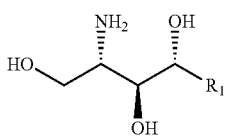
(XIV)

via a step of protection of the free amino group by protecting group $PG_2$,
wherein $R_1$ and $PG_2$ are as defined in formula (XIII).

According to one embodiment, the compound of formula (XIV) is of formula (XIVa):

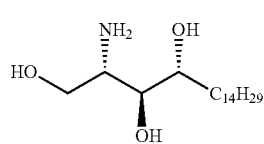
(XIVa)

Compound (XIVa) is called phytosphingosine, and is commercially available, notably from Tokyo Chemical Industry Co.

The preparation of a compound of formula (III) from a compound of formula (XIV) can be adapted from the method cited in Zhou, X. T.; Forestier, C.; Goff, R. D.; Li, C.; Teyton, L.; Bendelac, A.; Savage, P. B. Org. Lett. 2002, 4, 1267-1270.

According to one embodiment, the compound $R_2COCl$ (VII) is obtained from a compound of formula $R_2COOH$ (VIIa), wherein $R_2$ is as described in formula (I), via the transformation of the —COOH group into a —COCl group.

According to one embodiment, this step is carried out in the presence of thionyl chloride.

According to one embodiment, this step is carried out in a solvent, such as toluene.

According to one embodiment, this step is carried out at a temperature comprised from 50° C. to 100° C., preferably at 95° C.

The present invention also relates to a method of preparation of a compound of formula (I):

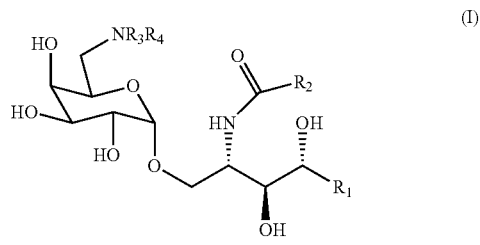
(I)

comprising:
a step a) of glycosylation, preferably in the presence of a Lewis acid, of a compound of formula (II):

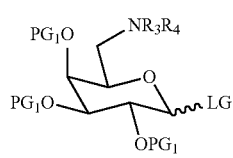
(II)

with a compound of formula (III):

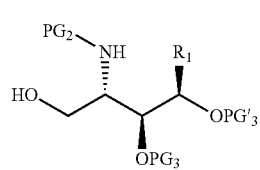
(III)

providing a compound of formula (IV):

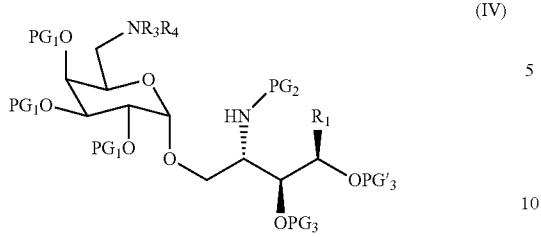
(IV)

a step b) of deprotection of the protecting groups $PG_1$ and $PG_2$ of said compound of formula (IV), preferably by hydrogenolysis in the presence of a metal catalyst, providing a compound of formula (V):

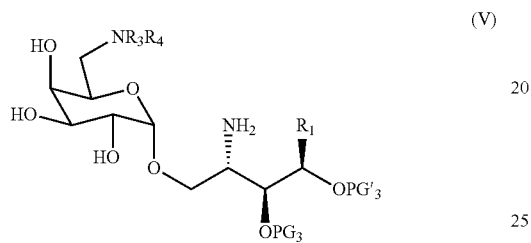
(V)

a step c) of coupling of said compound of formula (V), with a compound of formula $R_2COCl$ (VII), in the presence of a base, and a step d) of deprotection of the protecting groups $PG_3$ and $PG'_3$ of the product obtained in step c), providing a compound of formula (I), wherein $PG_1$, $PG_2$, $PG_3$, $PG'_3$, $R_1$, $R_2$, $R_3$, and $R_4$ are as defined above in formula The present invention also relates to a method of preparation of a compound of formula (I):

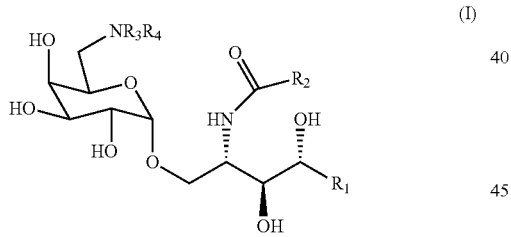
(I)

comprising:
a step a) of glycosylation, preferably in the presence of a Lewis acid, of a compound of formula (II):

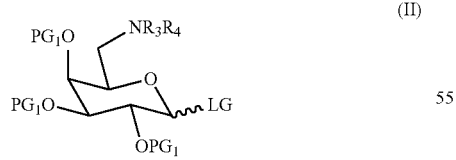
(II)

with a compound of formula (III):

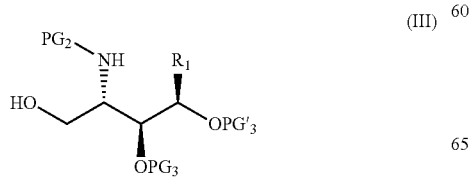
(III)

providing a compound of formula (IV):

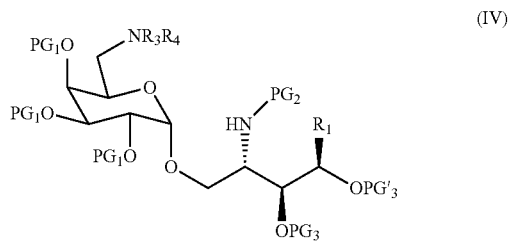
(IV)

a step b') of deprotection of the protecting groups $PG_1$, $PG_2$, $PG_3$ and $PG'_3$ of said compound of formula (IV), preferably by hydrogenolysis in the presence of a metal catalyst, optionally followed by a treatment in acidic conditions, providing a compound of formula (VI):

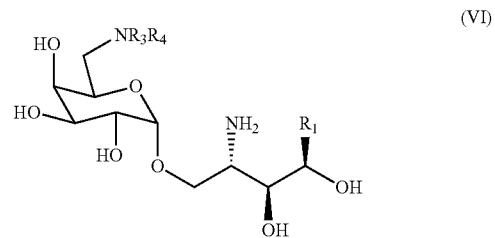
(VI)

a step c') of coupling of a compound of formula (VI) with a compound of formula $R_2COCl$ (VII), in the presence of a base, said step c') providing a compound of formula (I).

Preparation of Compound (Ia)

The present invention also relates to a method of preparation of a compound of formula (Ia):

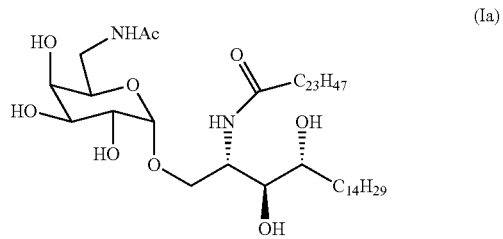
(Ia)

comprising:
a step a) of glycosylation, preferably in the presence of a Lewis acid, of a compound of formula (IIa):

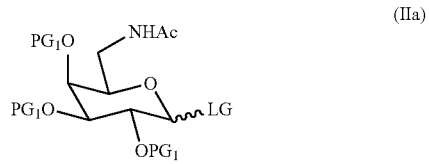
(IIa)

with a compound of formula (IIIa):

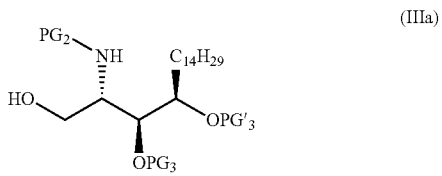
(IIIa)

providing a compound of formula (IVa):

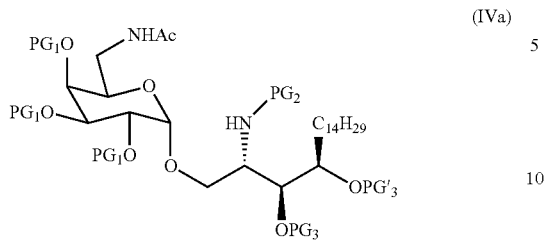
(IVa)

a step b) of deprotection of the protecting groups $PG_1$ and $PG_2$ of said compound of formula (IVa), preferably by hydrogenolysis in the presence of a metal catalyst, providing a compound of formula (Va):

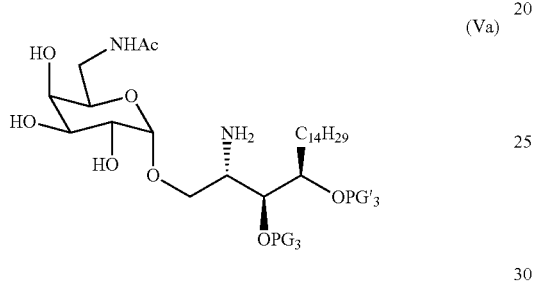
(Va)

a step c) of coupling of said compound of formula (Va), with a compound of formula $C_{23}H_{47}COCl$ (VIIa), in the presence of a base, and a step d) of deprotection of the protecting groups $PG_3$ and $PG'_3$ of the product obtained in step c), providing a compound of formula (Ia), wherein LG, $PG_1$, $PG_2$, $PG_3$ and $PG'_3$ are as defined above in formula (I).

The present invention also relates to a method of preparation of a compound of formula (Ia):

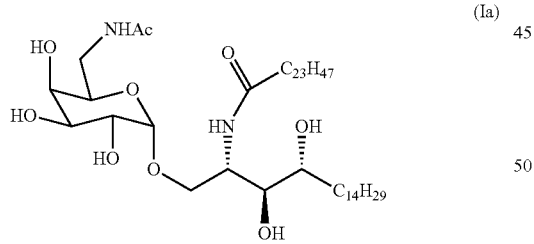
(Ia)

comprising:

a step a) of glycosylation, preferably in the presence of a Lewis acid, of a compound of formula (IIa):

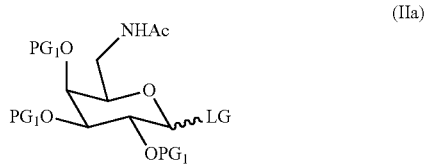
(IIa)

with a compound of formula (IIIa),

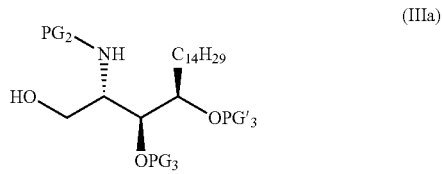
(IIIa)

providing a compound of formula (IVa):

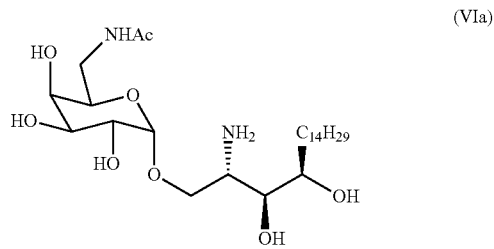
(IVa)

a step b') of deprotection of the protecting groups $PG_1$, $PG_2$, $PG_3$ and $PG'_3$ of said compound of formula (IVa), preferably by hydrogenolysis in the presence of a metal catalyst, optionally followed by a treatment in acidic conditions, providing a compound of formula (VIa):

(VIa)

a step c') of coupling of a compound of formula (VIa) with a compound of formula $C_{23}H_{47}COCl$ (VIIa), in the presence of a base, said step c') providing a compound of formula (Ia), wherein LG, $PG_1$, $PG_2$, $PG_3$ and $PG'_3$ are as defined above in formula (I).

According to one embodiment, the Lewis acid is TMSOTf.

According to one embodiment, the metal catalyst is $Pd(OH)_2$.

According to one embodiment, the base is triethylamine.

According to one embodiment, LG is a trichloroacetimidate group.

According to one embodiment, $PG_1$ is a benzyl group (-Bn).

According to one embodiment, $PG_2$ is a group of formula —C(O)OCH$_2$-Ph.

According to one embodiment, $PG_3$ and $PG'_3$ form together with the two oxygen atoms to which they are connected, an isopropylidene acetal group.

According to one embodiment, the method of preparation of a compound of formula (I) from a compound of formula (II) and a compound of formula (III) only comprises two steps of purification by silica-gel column chromatography.

According to one embodiment, the method of the invention comprises a first step of purification by silica-gel column chromatography after step a), and before step b) or step b').

According to one embodiment, the method of the invention comprises a second step of purification by silica-gel column chromatography after step c').

According to another embodiment, the method of the invention comprises a second step of purification by silica-gel column chromatography after step d).

The method of preparation of the invention enables the preparation of a compound of formula (Ia):

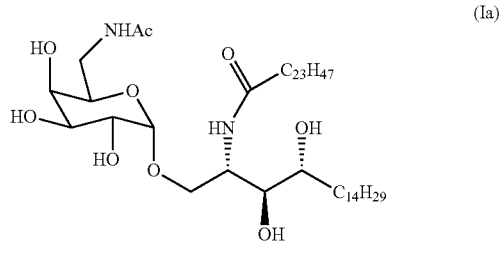

(Ia)

from a compound of formula (IIa):

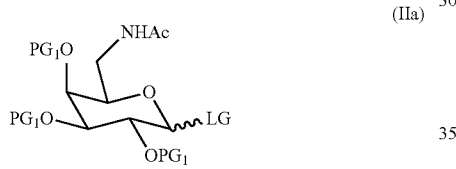

(IIa)

and a compound of formula (IIIa):

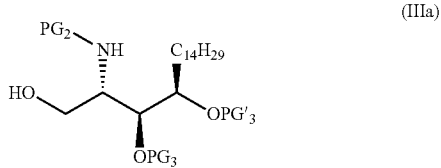

(IIIa)

by a sequence of reaction comprising only two steps of purification by silica-gel column chromatography.

Examples

Method of Preparation of Compound (Ia)

A batch of (Ia) was prepared in accordance with Good Manufacturing Practice for use in clinical trials. A narrative description of the synthesis steps is given below.

Preparation of Compound 1

Methyl 6-acetamido-2,3,4-tri-O-benzyl-α-D-galactopyranoside (1) was produced after 7 synthesis steps, from the commercially available (Indofine Chemical Company) 1,2,3,4-di-O-isopropylidene-α-D-galactopyranose (XII):

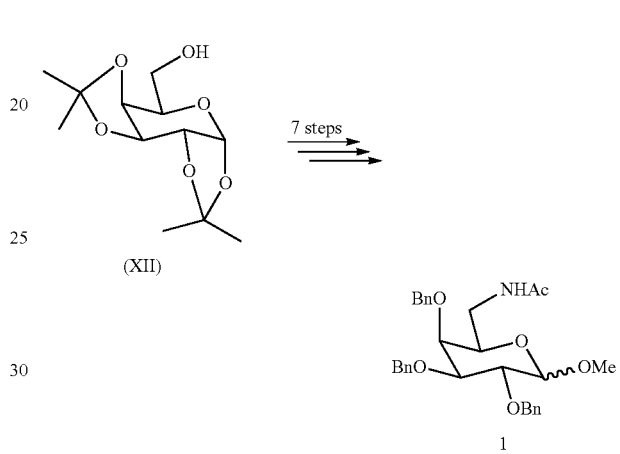

activation of the alcohol function as a tosyl group, from the commercially available (XII), substitution of the tosyl group by a phtalimide moiety, cleavage of the alcohols protecting isopropylidene groups, methylation of the anomeric position and purification on silica gel, cleavage of the phtalimide ring to provide free amine, acetalization of the alcohols and amino groups, cleavage of acetyl esters, and benzylation of hydroxyl groups and final purification on silica gel to provide compound 1.

A method of preparation of 1 from compound (XII) is described in the following scheme:

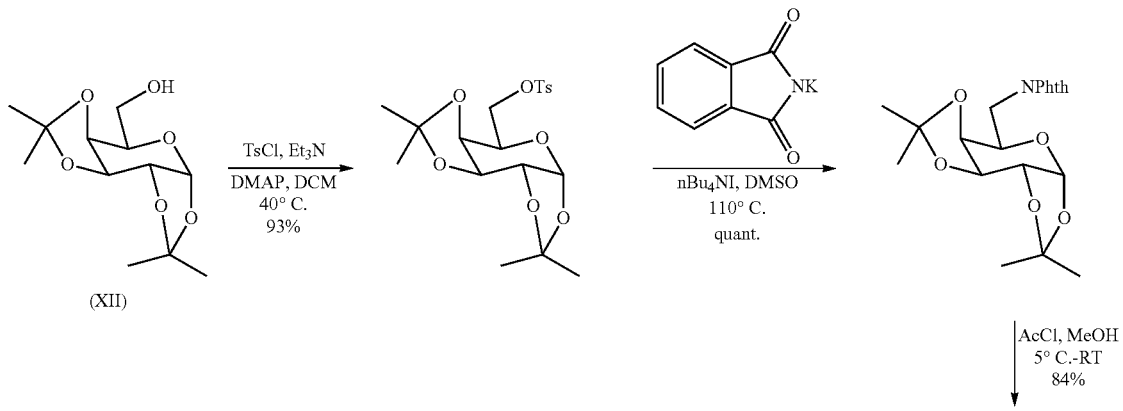

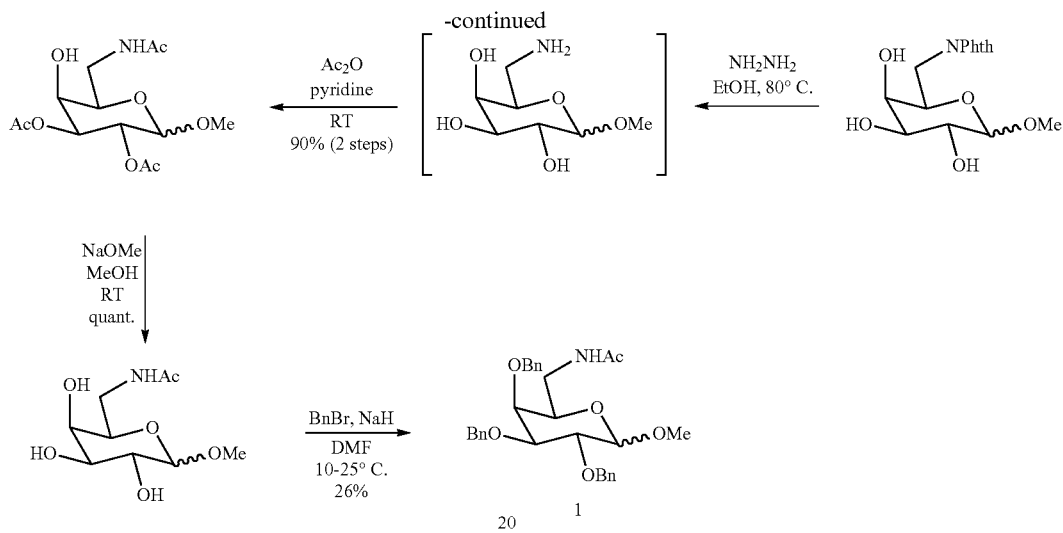

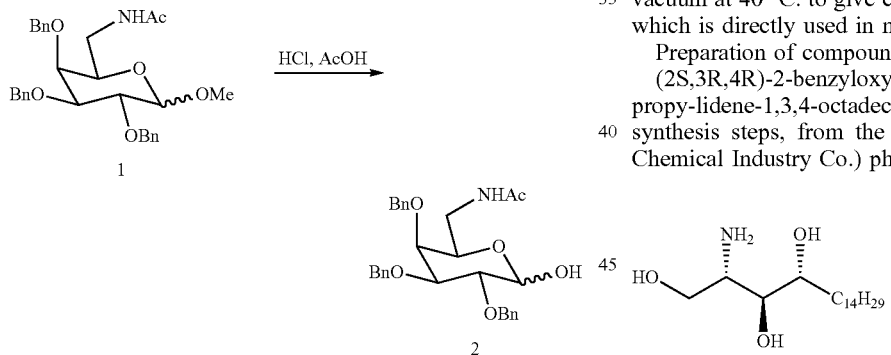

Compound (XII) is treated with tosylchloride in dichloromethane with triethylamine and dimethylamino pyridine to give the corresponding tosylate in 91% yield. The tosylate is treated with potassium phthalimide in DMSO with tetrabutylammonium iodide to give the corresponding phthalimide in approximately 100% yield. The phthalimide is treated with acetyl chloride in methanol to cause deprotection of the alcohols and formation of the methyl glycoside in 87% yield. The amine is then liberated by treating the phthalimide with hydrazine in ethanol. The amine is protected in the presence of acetic anhydride and pyridine and the alcohols are deprotected by treating the resulting compound with sodium methylate in methanol. The alcohol moieties are then protected with benzyl groups to yield compound 1.

Preparation of Compound 2

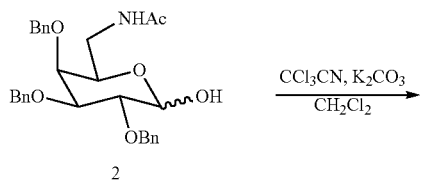

Compound 1 (1.0 eq), acetic acid and 6 N hydrochloric acid are successively added to an appropriate flask at room temperature. The reaction mixture is then heated at 75° C. and monitored by HPLC. After cooling to room temperature, dichloromethane and then water are added with stirring. After decantation and separation of the organic layer, the aqueous layer is re-extracted with dichloromethane. The organic layers are pooled and concentrated under vacuum at 40° C. to give crude compound 2 as a brown oily product which is used directly in the next operation.

Preparation of Compound 3

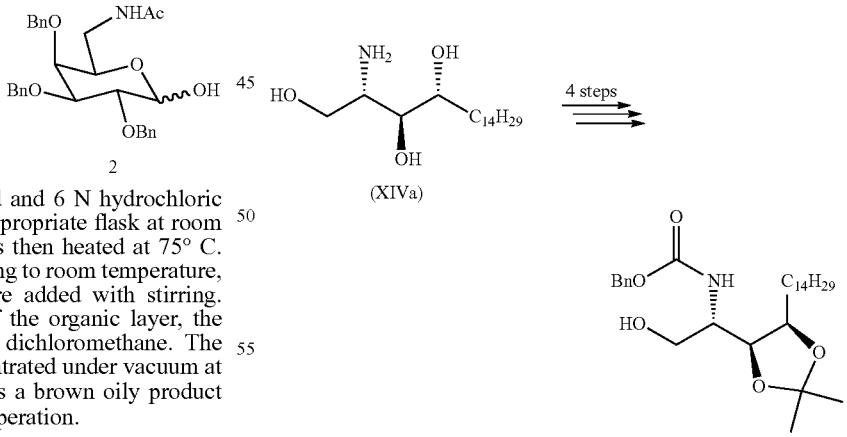

The oil 2 is dissolved in dichloromethane, and trichloroacetonitrile (10.0 eq) and potassium carbonate (5.0 eq) are successively added at room temperature. The reaction mixture is stirred at room temperature for at least 12 hours and then filtered on celite. The filtrate is concentrated under vacuum at 40° C. to give crude compound 3 as a brown oil which is directly used in next operation.

Preparation of compound 4

(2S,3R,4R)-2-benzyloxycarbonylamino-3,4-di-O-isopropy-lidene-1,3,4-octadecanetriol (4) was produced after 4 synthesis steps, from the commercially available (Tokyo Chemical Industry Co.) phytosphingosine (XIVa):

protection of the amino function as a carboxybenzyl group, from the commercially available (XIVa),
protection of the primary alcohol as a silylated ester,
protection of both secondary alcohols as an isopropylidene group,
cleavage of the silylated ester and final purification on silica gel to provide compound 4.

A method of preparation of 4 from compound (XIVa) is described in the following scheme:

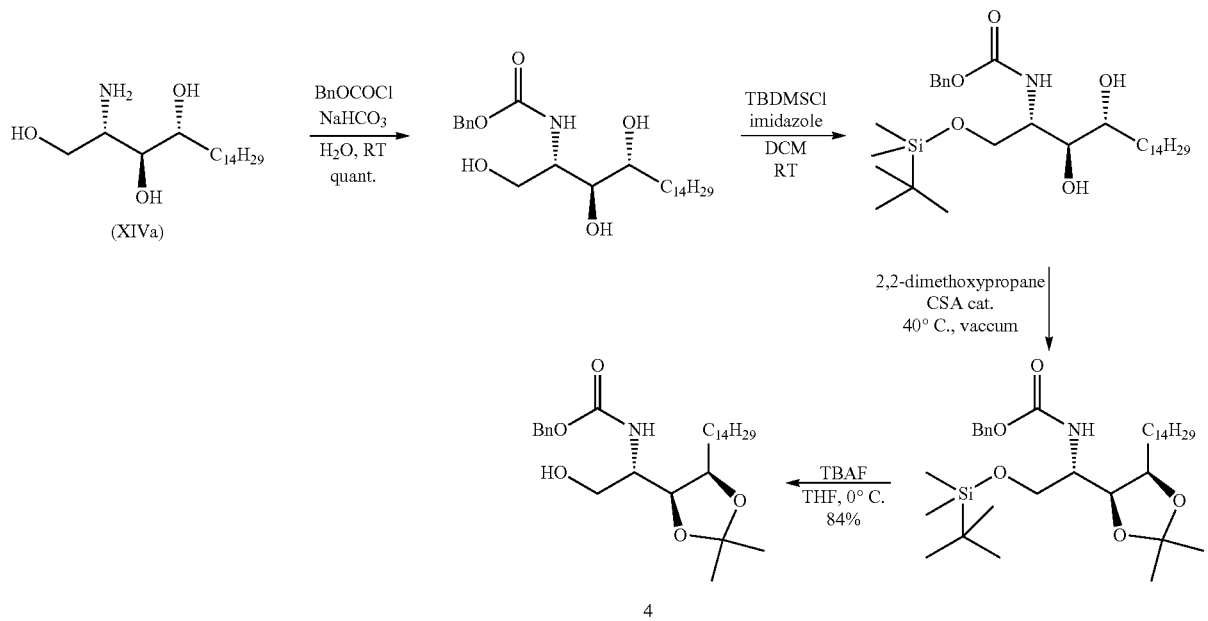

Phytosphingosine (XIVa) is reacted with benzyloxychloride in water and acetone with sodium bicarbonate to give the corresponding benzylcarbamate in 92% yield. The primary alcohol is protected by reaction with TBDMSCl in dichloromethane with imidazole to give the corresponding silylether in 94% yield. The secondary alcohols are protected by reaction with 2,2-dimethoxypropane with tosic acid to give the corresponding acetonide in 92% yield. The silylether protecting group is removed by treatment with tetrabutylammonium floride in THF to give alcohol 4 in 84% yield.

Preparation of Compound 5

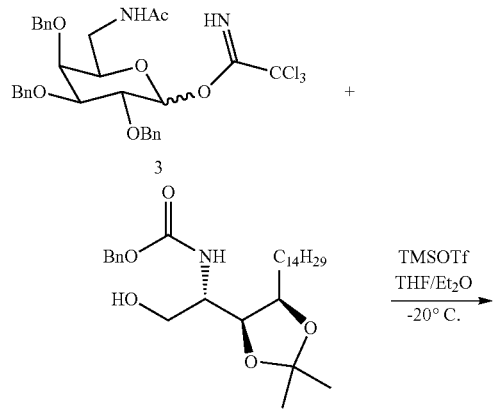

Under nitrogen, crude compound 3 (1.3 eq), THF, compound 4 (1.0 eq) and diethylether are successively added at room temperature to an appropriate flask. Activated 4A Molecular sieve (1.5 eq w/w with respect to compound 3) is added. The reaction mixture stirred under nitrogen at room temperature for at least one hour and then cooled to −20° C. Trimethylsilyltrifluoromethanesulfonate (0.6 eq) is added dropwise and the reaction mixture is stirred for at least one hour at −20° C., then quenched by addition of triethylamine (2.0 eq). The resulting suspension is allowed to reach room temperature slowly, then filtered on celite. The filtrate is concentrated under vacuum at 40° C. and solubilized in dichloromethane, washed with water and concentrated again under vacuum at 40° C. to give crude compound 5 as a brown oil.

This compound is solubilised in dichloromethane and a solid deposit on silica gel is realized. The product is then purified by chromatography on silica gel, using a mixture of cyclohexane and ethyl acetate (9/1 to 6/4, v/v) for elution. After concentration under vacuum at 40° C. of the fractions containing the pure product 5, compound 5 is obtained as a pale yellow solid.

Preparation of Compound 6

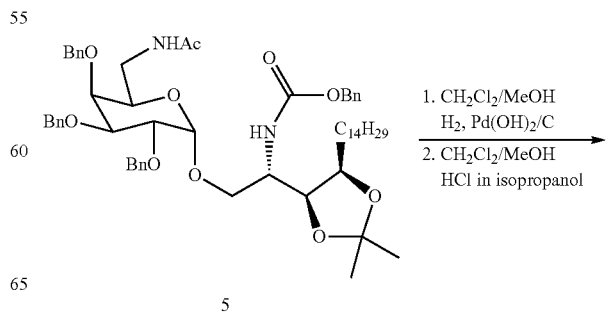

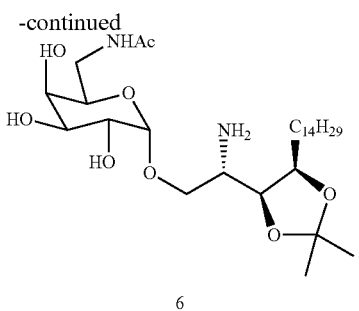

Compound 5 (1.0 eq), dichloromethane, methanol and palladium hydroxide 20% on charcoal, 50% wet (0.5 eq w/w) are successively added to an appropriate reactor. The reaction mixture is purged with nitrogen, then put under a hydrogen atmosphere (1 bar) at room temperature until completion of the reaction, which is monitored by HPLC. After filtration on celite to remove the catalyst, the filtrate is concentrated under vacuum at 25° C. to give a white solid.

To this white solid (1.0 eq), dichloromethane and methanol are added in an appropriate flask. 5N hydrogen chloride in isopropanol (5.0 eq) is added and the reaction mixture heated under stirring at 40° C. for 15 minutes and then concentrated under vacuum. The extent of hydrolysis is determined by HPLC. After drying compound 6 is obtained as a yellow solid.

Preparation of Compound 7

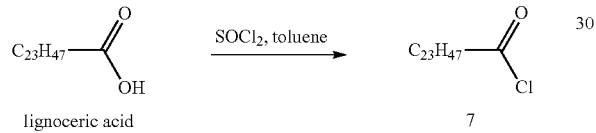

Lignoceric acid (1.0 eq, commercially available), toluene and thionyl chloride (5.0 eq) are successively added to an appropriate flask at room temperature. The reaction mixture is heated to 95° C. and then concentrated under vacuum at 50° C. After three co-evaporations with toluene and drying, compound 7 is obtained as a pale brown solid.

Preparation of Compound (Ia)

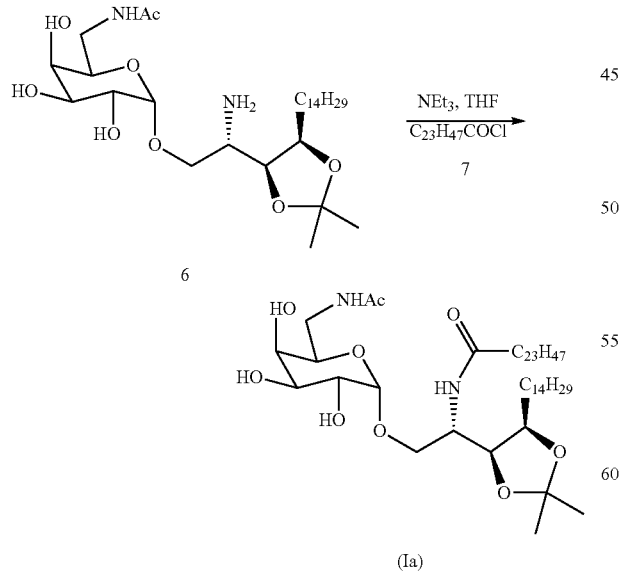

Compound 6 (1.0 eq) is mixed with THF in an appropriate flask. Triethylamine (2.5 eq) and compound 7 (0.9 eq) are successively added at room temperature. The reaction mixture is stirred at room temperature for at least one hour and monitored by HPLC. A mixture of dichloromethane and methanol (1:1 (v/v)) is added and the reaction mixture is concentrated under vacuum at 40° C. to give crude compound (Ia).

The crude product is solubilized in dichloromethane:methanol (1:1 (v/v)) and a solid deposit on silica gel prepared. The product is then purified by chromatography on silica gel, using a mixture of dichloromethane and methanol (9:1 to 7:3 (v/v)) for elution.

After concentration at 40° C. of the fractions containing pure compound (Ia), the resulting solid is warmed in a minimum volume of methanol:THF 9:1 (v/v) and after solubilisation, it is hot-filtered. The product is precipitated at room temperature and the solid is filtered, washed with methanol and dried at 35° C. The resulting solid is washed with ppi water before drying at 35° C.

Compound (Ia) is then obtained as a white solid.

The invention claimed is:
1. A method of preparation of a compound of formula (I):

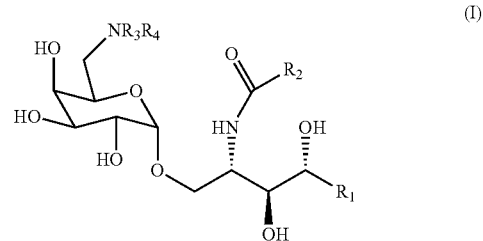

said method comprising:
a) glycosylating a compound of formula (II):

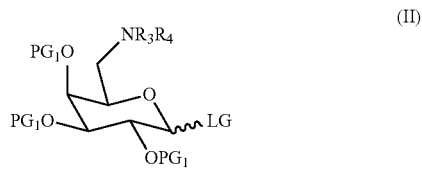

with a compound of formula (III):

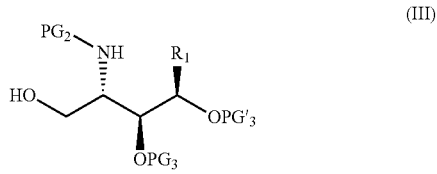

thereby producing a compound of formula (IV):

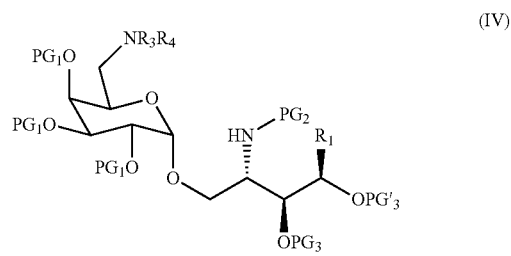

wherein:
- $R_1$ represents a linear or branched, saturated or unsaturated $C_1$-$C_{20}$ alkyl group;
- $R_2$ represents a linear or branched, saturated or unsaturated $C_1$-$C_{30}$ alkyl group;
- $R_3$ represents $C_1$-$C_6$ alkyl, a $C_3$-$C_6$ cycloalkyl, a $C_1$-$C_6$ acyl or a benzoyl group; and $R_4$ represents H or $C_1$-$C_6$ alkyl group; or
- $R_3$ and $R_4$ form together with the nitrogen atom to which they are attached a $C_2$-$C_6$ heterocycloalkyl group or a $C_1$-$C_5$ heteroaryl group;
- $PG_1$ represents a hydroxyl function protecting group;
- $PG_2$ represents a primary amine function protecting group selected from the group consisting of carboxybenzyl (Cbz), p-methoxybenzyl carbonyl (Moz or MeOZ), tert-butyloxycarbonyl (BOC), 9-fluorenylmethyloxycarbonyl (FMOC), acetyl (Ac), benzoyl (Bz), benzyl (Bn), carbamate groups, p-methoxybenzyl (PMB), 3,4-dimethoxybenzyl (DMPM), p-methoxyphenyl (PMP), tosyl (Ts) and other sulfonamides (Nosyl & Nps) groups;
- $PG_3$ represents a hydroxyl function protecting group;
- $PG'_3$ represents a hydroxyl function protecting group; and
- LG represents a leaving group; and said method further comprising, after step a):
b) deprotecting protecting groups $PG_1$ and $PG_2$ of the compound of formula (IV), said step b) providing a compound of formula (V):

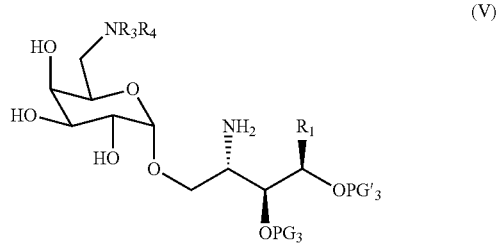

(V)

wherein $R_1$, $R_3$, $R_4$, $PG_3$ and $PG'_3$ are as defined above, and c) coupling the compound of formula (V) with a compound of formula $R_2COCl$ (VII), wherein $R_2$ represents a linear or branched, saturated or unsaturated $C_1$-$C_{30}$ alkyl group, in the presence of a base; and d) deprotecting protecting groups $PG_3$ and $PG'_3$ of the product obtained in step c);

said steps providing a compound of formula (I);
or
b') deprotecting protecting groups $PG_1$, $PG_2$, $PG_3$ and $PG'_3$ of compound of formula (IV), said step b') providing a compound of formula (VI):

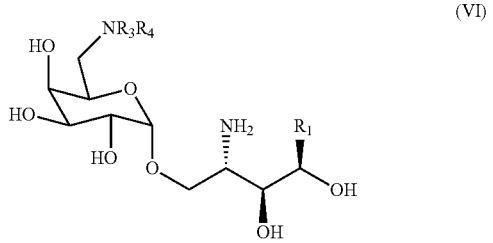

(VI)

wherein $R_1$, $R_3$ and $R_4$ are as defined above; and c') coupling the compound of formula (VI) with a compound of formula $R_2COCl$ (VII), wherein $R_2$ represents a linear or branched, saturated or unsaturated $C_1$-$C_{30}$ alkyl group, in the presence of a base, said step c') providing a compound of formula (I); to produce the compound of formula (I), wherein the method comprises no less than two and no more than two steps of purification by silica-gel column chromatography.

2. The method according to claim 1, wherein LG is a trichloroacetimidate group.

3. The method according to claim 1, wherein $R_1$ is a linear saturated $C_1$-$C_{20}$ alkyl group.

4. The method according to claim 1, wherein $R_2$ is a linear saturated $C_1$-$C_{20}$ alkyl group.

5. The method according to claim 1, wherein:
$R_3$ is an acyl group; and
$R_4$ is H.

6. The method according to claim 1, wherein protecting group $PG_1$ is a benzyl group.

7. The method according to claim 1, wherein protecting group $PG_2$ is a carboxybenzyl group.

8. The method according to claim 1, wherein the protecting groups $PG_3$ and $PG'_3$ form together with the two oxygen atoms to which they are connected, an isopropylidene acetal group.

9. The method according to claim 5, wherein $R_3$ is an acyl group of formula —C(O)CH$_3$.

10. The method according to claim 1, wherein a first of the two steps of purification by silica-gel column chromatography occurs between steps (a) and (b).

11. The method according to claim 10, wherein step (c'), after step (b'), is performed by coupling of a compound of formula (VIa):

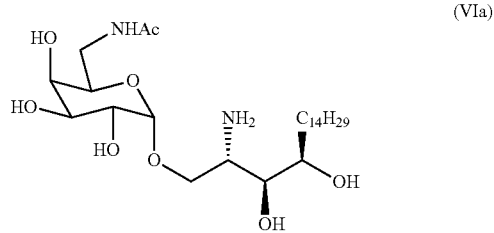

(VIa)

with a compound of formula $C_{23}H_{47}COCl$ (VIIa), in the presence of a base, thereby providing a compound of formula (Ia),

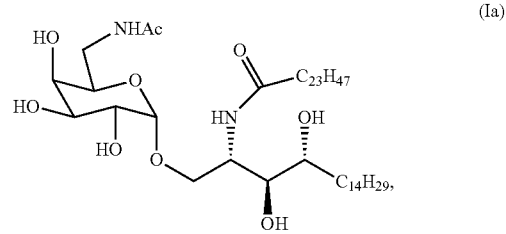

(Ia)

wherein a second of the two steps of purification occurs after step (c).

12. The method according to claim 10, wherein step (c), after step (b), is performed by coupling of a compound of formula (Va)

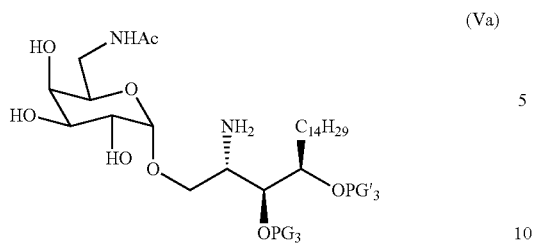
(Va)
with a compound of formula $C_{23}H_{47}COCl$ (VIIa), in the presence of a base, thereby providing a compound of formula (Ia)
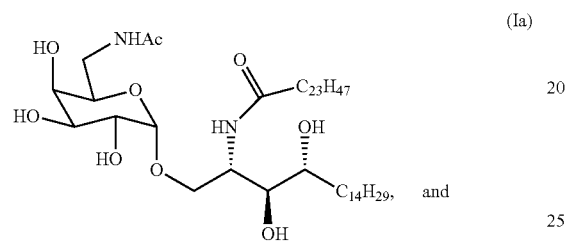
(Ia)
wherein a second of the two steps of purification occurs after step (d).
* * * * *